(12) United States Patent
Lin

(10) Patent No.: US 7,469,792 B1
(45) Date of Patent: Dec. 30, 2008

(54) CONTAINER AND RACK SYSTEM

(76) Inventor: Peter Lin, 345 Ivyland Rd., Warminster, PA (US) 18974-2205

( * ) Notice: Subject to any disclaimer, the term of this patent is extended or adjusted under 35 U.S.C. 154(b) by 572 days.

(21) Appl. No.: 10/968,409

(22) Filed: Oct. 18, 2004

(51) Int. Cl.
*A47B 73/00* (2006.01)
(52) U.S. Cl. .......................................... 211/74
(58) Field of Classification Search ............... 211/74, 211/181.1, 133.5, 132.1, 85.31, 71.01; 206/139, 206/561, 174, 562, 168; 229/934; 220/486, 220/509
See application file for complete search history.

(56) References Cited

U.S. PATENT DOCUMENTS

| | | | | |
|---|---|---|---|---|
| 1,514,375 A | * | 11/1924 | Crimmel | 211/74 |
| 1,947,932 A | * | 2/1934 | Fante | 211/85.4 |
| 3,858,835 A | * | 1/1975 | Baren | 248/94 |
| 3,955,682 A | * | 5/1976 | Baren | 211/74 |
| 4,350,253 A | * | 9/1982 | Rusteberg | 211/74 |
| 5,150,784 A | * | 9/1992 | Sayad | 206/202 |
| 5,785,189 A | * | 7/1998 | Gollob et al. | 211/187 |
| 6,003,692 A | * | 12/1999 | Kozak | 211/74 |
| 6,173,845 B1 | * | 1/2001 | Higgins et al. | 211/74 |

* cited by examiner

*Primary Examiner*—Sarah Purol
(74) *Attorney, Agent, or Firm*—LaMorte & Associates

(57) ABSTRACT

A rack and container assembly and the associated method of holding the containers in the rack. The rack has frame elements that define at least one slot of a first width. The frame elements are rounded in cross-section having a first radius of curvature. Each of the containers has an exterior surface of a second width that is greater than the width of the slots in the rack. An arcuate groove is formed in the exterior surface of each container. The arcuate grooves enable the containers to pass into the slots. Each arcuate groove has a cross-section with a second radius of curvature that is at least as large as the first radius of curvature of the frame elements that form the slot. When the containers are placed in the slots, the only area of the containers that physically contacts the rack is the shallow area of the arcuate groove.

11 Claims, 4 Drawing Sheets

CONTAINER AND RACK SYSTEM

BACKGROUND OF THE INVENTION

1. Field of the Invention

In general, the present invention relates to containers that are designed to hold biologically active materials. More particularly, the present invention relates to the external structure of such containers and features of such containers that enable them to be supported within the confines of an autoclave for sterilization.

2. Description of the Prior Art

In the pharmaceutical industry, many biologically active compounds are routinely handled by scientists, lab technicians, quality control testers and the like. Some of these biologically active compounds are alive, in the form of bacteria, virus, molds and cell components. When these materials are tested, sampled or otherwise transported, the biologically active compounds are typically placed into stainless steel containers. The volume of the stainless steel containers can vary widely from a single ounce to many gallons.

The stainless steel containers used to transport biologically active compounds typically do not use threaded closures. Threaded closures provide confined areas between threads that may harbor contaminants. Due to the physical shape of the threads, it is very difficult to properly clean threads to the sanitary standards needed. It is for this reason that threaded closures are generally not used. Rather, what are used are flanged caps that are joined to the container with a clamp. The containers, the caps and the clamps are typically made from stainless steel so that all components can be sanitized in an autoclave prior to and after use. In this manner, the container, cap and clamp can be kept sterile so as not to introduce harmful contamination into the pharmaceutical product being transported or stored.

Containers that are designed to hold small volumes of material, i.e. less than one pint, often have weighted bottoms. This helps prevent the container from inadvertently tipping when resting on a surface. However, it also makes such small containers bottom heavy, and the entire container is very heavy for its size.

A problem therefore occurs when such small containers are to be cleaned in an autoclave. To clean a container in an autoclave, the container must be inverted so that contaminants do not get trapped within the container. However, since the containers have weighted bottoms, the containers are top heavy when inverted and tend to fall over easily. Furthermore, the containers often have plain external features that are designed to not harbor contamination. The lack of external features make it difficult to set the containers into conventional autoclave racks. The relatively large weight of the containers also prevents many containers from being placed on a single conventional rack. Additionally, the containers cannot be stacked atop one another within an autoclave, or else the areas of abutment between the heavy containers may harbor contamination.

A need therefore exists for a new container and rack assembly that can be used in an autoclave, wherein the container has a structure that does not harbor contamination yet enables the container to engage a rack. And, wherein the rack itself can hold many containers in a confined space without having the containers abut and harbor contamination. This need is met by the present invention as described and claimed below.

SUMMARY OF THE INVENTION

The present invention is a rack and container assembly and the associated method of holding the containers in the rack. The rack has frame elements that define at least one slot of a first width. The frame elements that define each slot are rounded in cross-section having a first radius of curvature.

Each of the containers has an exterior surface of a second width that is greater than the width of the slots in the rack. An arcuate groove is formed in the exterior surface of each container. The arcuate grooves enable the containers to pass into the slots. Each arcuate groove has a cross-section with a second radius of curvature that is at least as large as the first radius of curvature of the frame elements that form the slot.

As a result, when the containers are placed in the slots, the only area of the containers that physically contacts the rack is the shallow area of the arcuate groove. The containers can, therefore, hang suspended from the rack and can be fully sterilized in an autoclave while held within the rack.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Although the present invention container and rack assembly can be made in any size, it is particularly useful for use with small volume containers of the type that are commonly sterilized using a tabletop autoclave. As a result, the selected embodiment of the present invention that is illustrated shows a container having a volume capacity of less than 250 milliliters. The rack is sized to fit within standard tabletop autoclaves and is shown holding four containers. The use of such exemplary sizes is set forth to present one of the best modes contemplated for the invention. The shown sizes should not be considered a limitation to the present invention.

Figure 1:
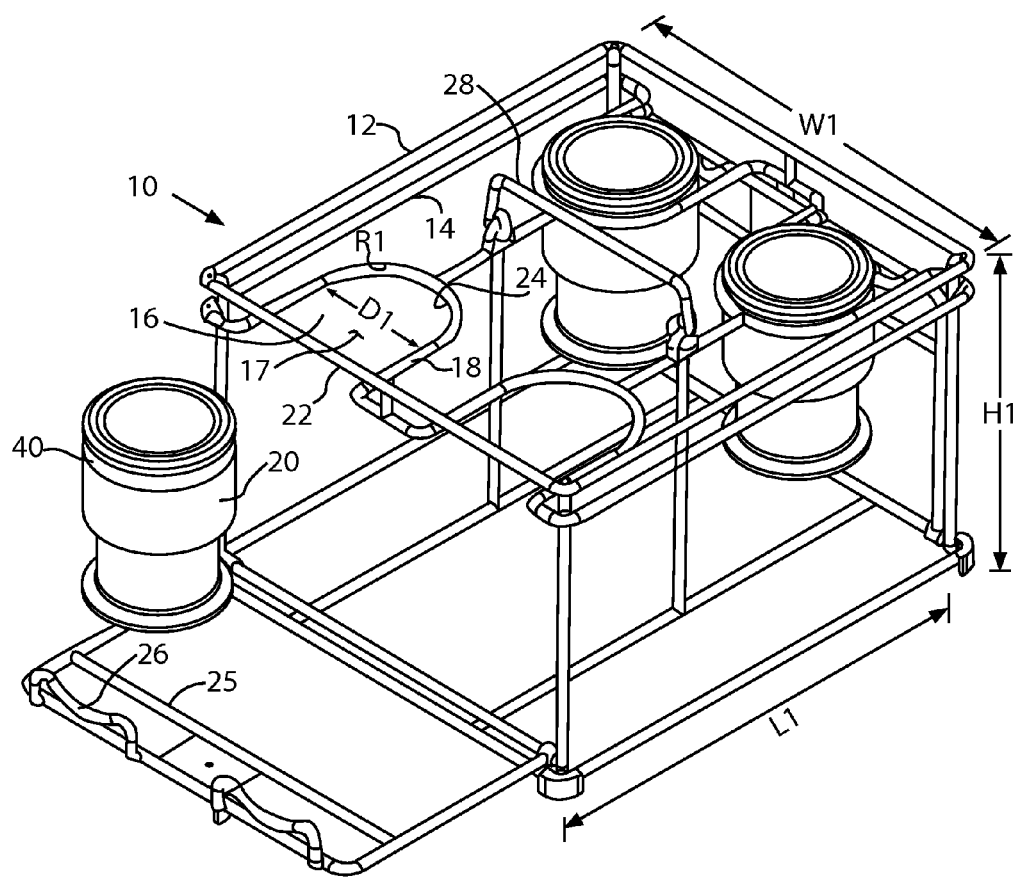
FIG. 1 is a perspective view of an exemplary embodiment of the present invention rack and container assembly.

Referring to FIG. 1, a container and rack assembly 10 are shown. The rack 12 holds up to four containers 20. The rack 12 holds the containers 20 so that the containers 20 are suspended from the rack 12 and do not abut. The rack 12 itself has a wire framework 14 made from stainless steel frame elements that have been bent and or welded together. Any weld used in the construction of the rack 12 is polished to remove any rough area that can harbor contaminants. The rack 12 has a length L1, width W1 and height H1. The length L1 is preferably between six inches and twelve inches. The width W1 and the height H1 are preferably smaller than the length L1. In this manner, the rack 12 can fit into most commercial autoclaves.

The rack 12 contains a plurality of U-shaped slots 16. Each of the U-shaped slots 16 defines a slot area 17 having a diameter D1. Each of the U-shaped slots 16 is also made from rounded wire frame elements 18 that have a small cross-sectional radius of curvature R1. The U-shaped slots 16 have an open mouth end 22 and a curved closed end 24. The open mouth end 22 of each of the U-shaped slots 16 faces outwardly toward a side wall 25 of the rack 12. The side walls 25 of the rack 12 that face the open mouth ends 22 of the U-shaped slots 16 can be selectively opened. The side walls 25 can be configured so that they can be selectively removed. However, in the shown embodiment, the side walls 25 are closures that can pivot between an open position and a closed position.

The side walls 25 have arcuate segments 26 that close the open mouth end 22 of the U-shaped slots 16 when the side walls 25 are in their closed positions. The arcuate segments 26 are made of the same gauge rounded frame elements as is the remainder of the U-shaped slots 16.

An optional handle 28 is provided at the top of the rack 12 to facilitate the carrying of the rack 12. The handle 28 is symmetrically centered between the U-shaped slots 16 so that the rack 12 is balanced when containers 20 are placed within the U-shaped slots 16.

Figure 2:
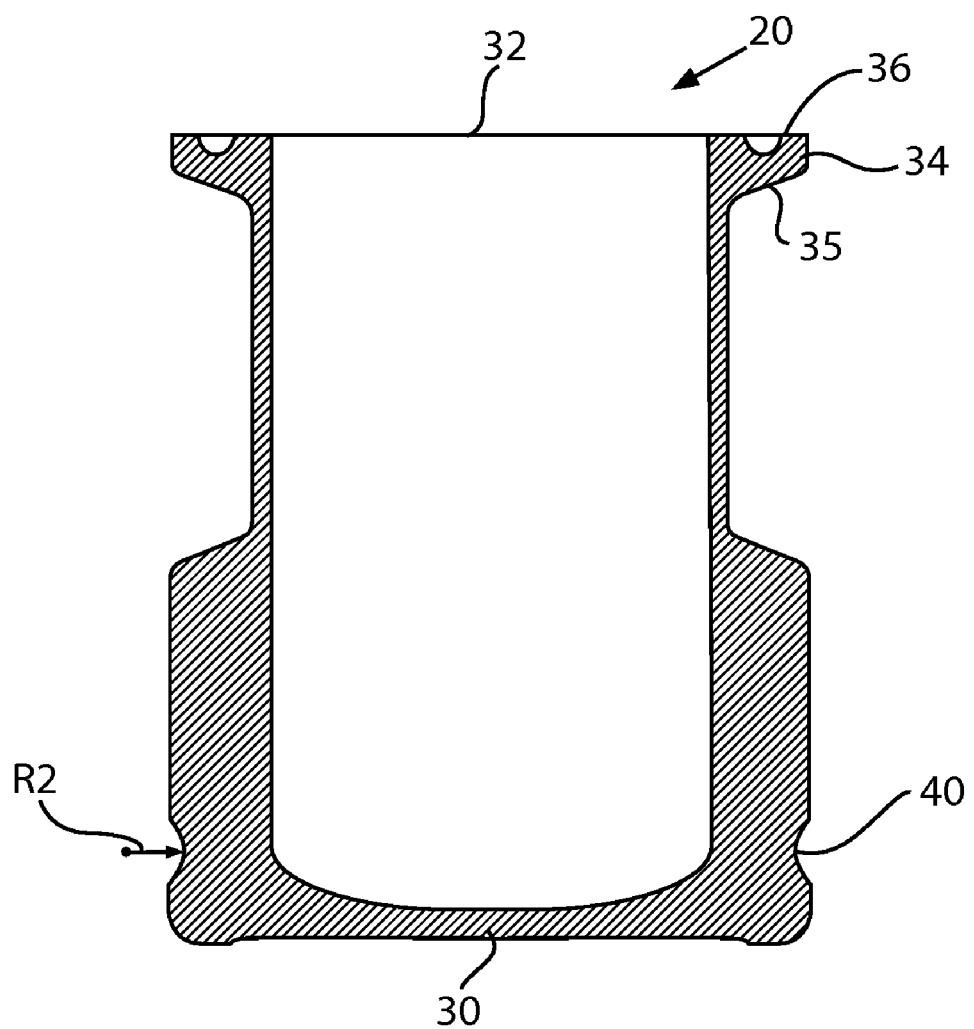
FIG. 2 is a cross-sectional view of a first exemplary embodiment of a container.

Referring briefly to FIG. 2, the structure of a container 20 is shown that can be held by the rack 12. The container 20 has a closed bottom end 30 and an open top end 32. A flange 34 radially extends about the open top end 32 of the container 20. The flange 34 has a sloped bottom surface 35. A groove 36 is formed on the top surface 37 of the flange 34. The groove 36 is sized to receive a sealing gasket 38. The sloped bottom surface 35 is sized to receive a pipe clamp, as will later be explained.

An arcuate groove 40 is formed on the exterior of the container 20, proximate its closed bottom end 30. The arcuate groove 40 encircles the container 20 in a continuous ring. The arcuate groove 40 has an arcuate cross-sectional profile. The radius of curvature R2 for the arcuate groove 40 is equal to or slightly greater than the radius of the rounded frame elements 18 (FIG. 1) used to form the U-shaped slots in the rack.

Returning to FIG. 1, it will now be understood that by inverting the containers 20, the arcuate groove 40 near the bottom of the containers 20 can be advanced into the U-shaped slots 16. As the containers 20 pass into the U-shaped slots 16, the rounded frame elements 18 defining the U-shaped slots 16 pass into the arcuate groove 40, therein preventing the containers 20 from being shaken or jarred out of the U-shaped slots 16. Once the side walls 25 of the rack 12 are closed, the arcuate segments 26 on the side walls 25 close the open mouth end 22 of the U-shaped slots 16 and the containers 20 are locked into the rack 12.

The containers 20 are supported in the rack 12 upside down. Thus, when the rack 12 and containers 20 are placed in an autoclave, the open containers 20 drain freely and do not harbor any contamination.

The arcuate groove 40 near the bottom of each container 20 is shallow. Thus, only a small percentage of the diameter of the rounded frame elements 18 that makes the U-shaped slots 16 pass into the arcuate groove 40. The area of abutment between the rack 12 and the containers 20 is therefore very small and is too exposed to retain any contamination. The rounded frame elements 18 used in the construction of the rack 12 have a very small cross-section compared to that of the container 20. The rounded frame elements 18 on the rack 12, therefore, quickly reach the temperature of the interior of the autoclave when within the autoclave. Consequently, any contamination touching the rack 12 between the rack 12 and the containers 20 is sterilized. The wire framework 14 of the rack 12 also allows the rack 12 to quickly cool to room temperature when removed from the autoclave. The handle 28 will therefore quickly cool and allow the sterile containers 20 to be transported without having to touch and potentially contaminate the containers 20.

Figure 3:
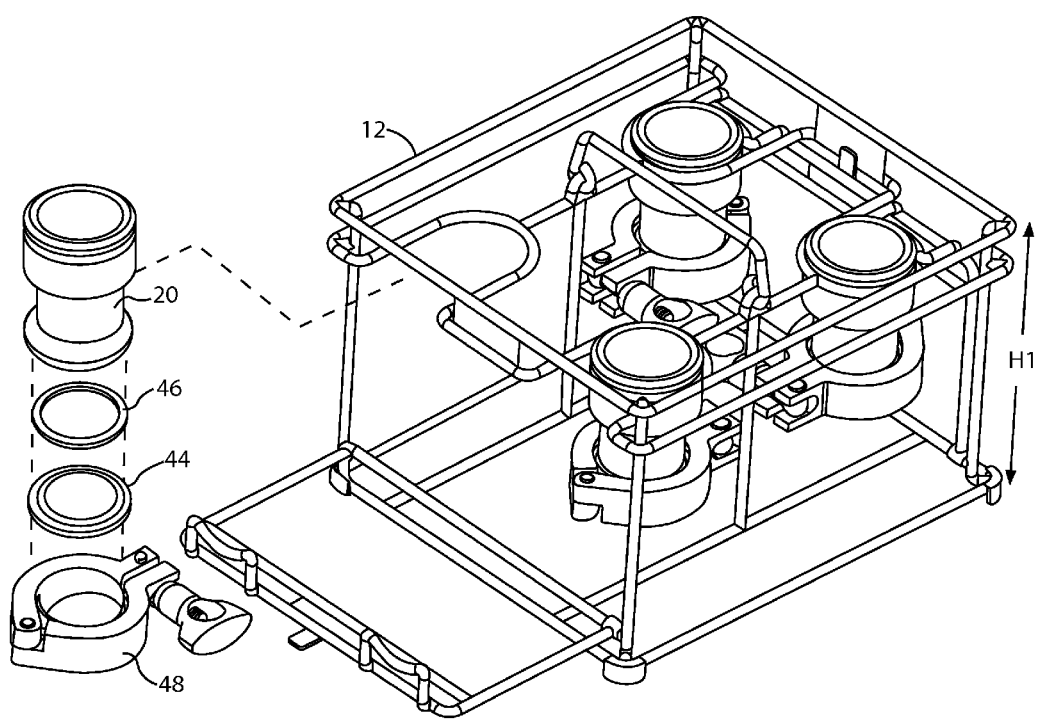
FIG. 3 is a perspective view of the embodiment of FIG. 1, having the containers sealed with caps and clamps.

Referring to FIG. 3, it can be seen that each of the containers 20 can be closed with a cap 44, a gasket 46 and a pipe clamp 48. The rack 12 is designed with a height H1, tall enough to support these elements. Thus, containers 20 filled with material and locked closed with pipe clamps 48 can be suspended from the rack 12. The rack 12 can then be used to transport the filled containers 20, or hold the filled containers in an oven or refrigerator.

Figure 4:
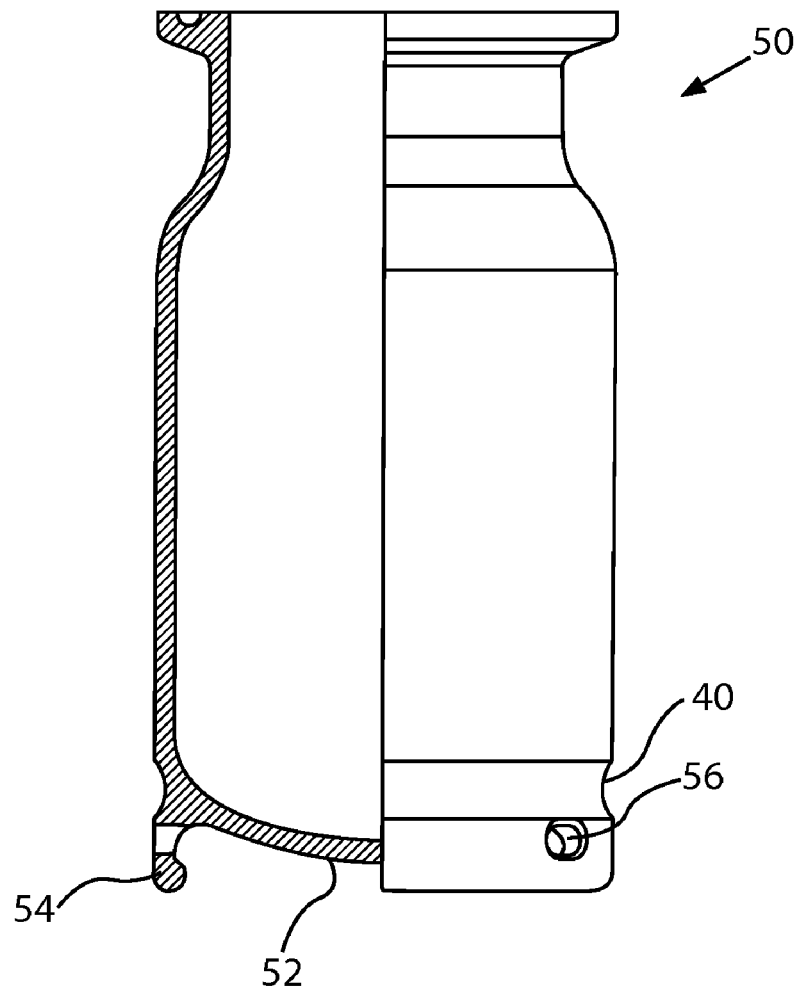
FIG. 4 is cross-sectional view of a second exemplary embodiment of a container.

In the shown embodiment, the containers 20 have flat bottom ends that enable the containers 20 to be free standing. However, when a flat bottom end is held inverted in the rack 12, it presents a surface upon which contaminates can puddle within an autoclave. Referring to FIG. 4, an alternate embodiment of a container 50 is shown that eliminates this problem. In the shown embodiment, the container 50 has a curved bottom surface 52. A cylindrical wall 54 extends below the curved bottom surface 52 from the peripheral edge of the curved bottom surface 52. The cylindrical wall 54 terminates in a flat plane. Drain holes 56 are formed in the cylindrical wall 54 along the junction between the cylindrical wall 54 and the curved bottom surface 52. Consequently, when the container 50 is inverted, any fluid that lands on, or forms within, the cylindrical wall 54 will immediately drain through the drain holes 56. No fluid will therefore accumulate on the curved bottom surface 52 within the area defined by the cylindrical wall 54.

The container 50 has the same arcuate groove 40 as has been previously described. It will therefore be understood that the container 50 can be hung within the previously described rack in the same manner as the container first described in FIG. 1.

It will be understood that the embodiments of the present invention that have been described are merely exemplary and that a person skilled in the art can make many variations to those embodiments. For example, the rack can be made to hold one or any plurality of containers. Furthermore, the rack and containers can be made in any size. What is important, it that the racks hold the containers so that the containers are only contacted in the grooves on the exterior of the containers. All such modifications, variations and alternate embodiments are intended to be included within the scope of the present invention as defined by the claims below.

What is claimed is:

1. An assembly, comprising:
   a rack having frame elements that define at least one slot of a first width, wherein said frame elements defining each said slot are rounded in cross-section having a first radius of curvature;
   at least one container, each said container having an open top, a closed bottom, and an exterior surface of a second width that is greater than said first width;
   an arcuate groove disposed in said exterior surface, wherein said arcuate groove is sized to pass into said slot and wherein said arcuate groove has a cross-section with a second radius of curvature that is at least as large as said first radius of curvature; and
   a cylindrical wall that extends below said closed bottom of said container, wherein drain holes are formed where said cylindrical wall meets said closed bottom.

2. The assembly according to claim 1, wherein said arcuate groove encircles said container.

3. The assembly according to claim 1, wherein said rack supports said at least one container in an elevated position so that said at least one container is suspended from said slot.

4. The assembly according to claim 1, wherein said rack has sides that can be selectively moved between an open position and a closed position.

5. The assembly according to claim 1, wherein said rack is comprised of an open wire framework.

6. The assembly according to claim 1, wherein said arcuate groove is formed around said body proximate said closed bottom.

7. The assembly according to claim 6, wherein each said container has a flange radially extending from said open top end, said flange having a top surface in which is formed an annular depression for receiving a gasket seal.

8. The assembly according to claim 1, wherein said closed bottom surface has a convex exterior surface.

9. The assembly according to claim 1, wherein each said container has an open top end and a closed bottom, wherein said arcuate groove is formed around said body proximate said closed bottom; and
   a pipe clamp flange radially extending from said exterior surface of said container body at said open top end, said flange having a top surface in which is formed an annular depression for receiving a gasket seal.

10. The assembly according to claim 9, further including a cylindrical wall that extends below said closed bottom, wherein drain holes are formed where said cylindrical wall meets said closed bottom.

11. The assembly according to claim 10, wherein said closed bottom has a convex exterior surface.

\* \* \* \* \*